(12) United States Patent  
Berry, Jr.

(10) Patent No.: US 6,654,991 B2  
(45) Date of Patent: Dec. 2, 2003

(54) TROCAR BUTTON

(76) Inventor: David L. Berry, Jr., 7481 White Birch La., Erie, PA (US) 16509

( * ) Notice: Subject to any disclaimer, the term of this patent is extended or adjusted under 35 U.S.C. 154(b) by 0 days.

(21) Appl. No.: 10/099,365

(22) Filed: Mar. 18, 2002

(65) Prior Publication Data

US 2003/0172503 A1 Sep. 18, 2003

(51) Int. Cl.[7] ................................................. A01N 1/00
(52) U.S. Cl. ................................ 27/21.1; 600/32
(58) Field of Search ........................ 27/21.1; 600/32

(56) References Cited

U.S. PATENT DOCUMENTS

| | | | | |
|---|---|---|---|---|
| 1,782,332 A | * | 11/1930 | Arnold | |
| 2,437,381 A | * | 3/1948 | Cullen | |
| 2,522,564 A | * | 9/1950 | Brown | |
| 2,804,072 A | * | 8/1957 | Genzer | |
| 2,850,788 A | * | 9/1958 | Rypysc | |
| 2,942,323 A | * | 6/1960 | Strickland | |
| 3,465,398 A | * | 9/1969 | Rector | |
| 3,613,188 A | * | 10/1971 | Muscott | |
| 5,403,336 A | * | 4/1995 | Kieturakis et al. | |
| 5,443,482 A | * | 8/1995 | Stone et al. | |
| 5,645,565 A | * | 7/1997 | Rudd et al. | |
| 5,901,424 A | * | 5/1999 | Rector | |
| 6,016,806 A | * | 1/2000 | Webb | |
| 6,082,362 A | * | 7/2000 | Webb | |

* cited by examiner

*Primary Examiner*—Dennis Ruhl  
(74) *Attorney, Agent, or Firm*—Richard K. Thomson

(57) ABSTRACT

A device to facilitate injection/extraction of fluids from cadaver's body cavities and to plug the incisions made to effect such injections/extractions. The trocar button of the present invention has both an external, manually operable drive surface and an internal drive surface engageable by a conventional insertion tool. Additionally, both the flange and the overall dimensions of the trocar button are increased to make it more user friendly.

10 Claims, 1 Drawing Sheet

TROCAR BUTTON

BACKGROUND AND SUMMARY OF THE INVENTION

The present invention is directed to a trocar button for use in preparing a body for burial. More particularly, the present invention is directed to a trocar button that has both an external drive to permit manual engagement for initial thread engagement and an internal drive for tool engagement to permit final seating of the button.

Trocar buttons are typically used in preparing a body for burial, being used for 1) draining fluid from body cavities, 2) injecting embalming fluid into those cavities and 3) in some instances, plugging incisions that have been formed for these and other purposes. Traditionally, these buttons have an internal drive orifice that is received on an insertion tool and are rotated so that an engagement thread can advance the trocar button through a small incision in the cadaver's skin. These buttons have a maximum outer diameter of ⅝" and can be difficult to manipulate, particularly in initial placement and starting the threads.

It is an object of the present invention to provide a more "user-friendly" trocar button. The trocar button of the present invention has a barrel-shaped entry tip having a diameter to facilitate insertion into a slit in the cadaver's skin. A conical body portion (which preferably has a conical angle of 45°) extends outwardly from a first end of the entry tip, the conical body portion having a threaded eternal peripheral section. A head section is attached to the body portion, the head portion having an external, manually-engageable drive and an internal drive which may be engaged by a tool, whereby the manually-engageable drive may be used to initiate insertion resulting from manual rotation and said trocar button may be fully seated by engaging a tool in said internal drive. The trocar button of the present invention has a maximum outer diameter of ⅞", fully 40% larger than conventional buttons. Further, the head section has a flange which extends from the maximum diameter of the conical section an amount of between 36 and 40% of the maximum diameter of the conical portion. This outwardly extending flange has a gear tooth pattern formed about its periphery permitting the flange to easily be grasped in the user's fingers and thread engagement manually initiated. The corners of each gear tooth are rounded to eliminate the risk of the gear teeth puncturing protective, elastic gloves. Once the rotation becomes more difficult as the flange approaches the surface of the cadaver's skin, the tool may be inserted in the internal drive and rotated to fully seat the trocar button in the orifice, with the flange flush with the skin to prevent bulges showing from underneath the clothes. The gear teeth do not extend all the way to the lower surface of the flange so that the gear teeth will not bite into the cadaver's skin thereby resisting rotation.

Various other features, advantages and characteristics of the present invention will be apparent to one of ordinary skill in the art after a reading of the following detailed description.

BRIEF DESCRIPTION OF THE DRAWINGS

The preferred embodiment(s) of the present invention are set forth in the drawings, like items bearing like reference numerals and in which.

DETAILED DESCRIPTION OF THE PREFERRED EMBODIMENT(S)

Figure 1:
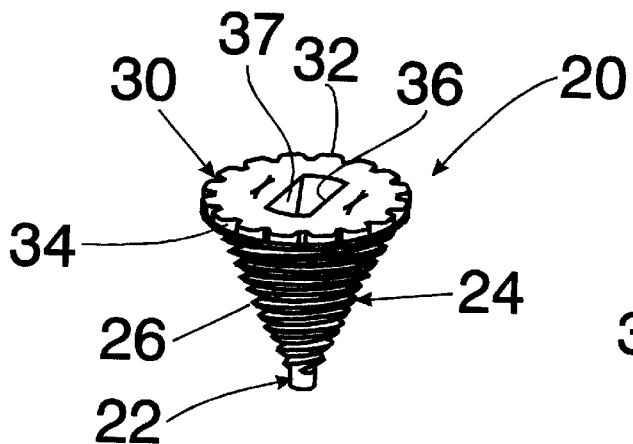
FIG. 1 is a perspective view of a first embodiment of the trocar button of the present invention.
Figure 2:
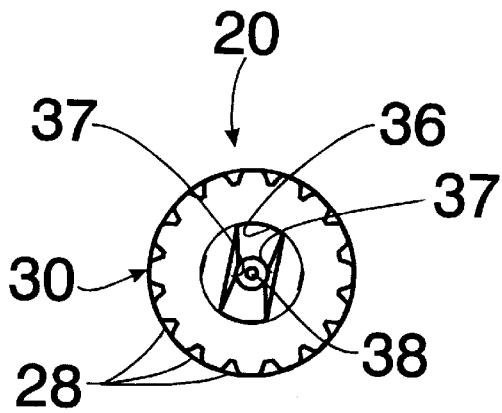
FIG. 2 is a top view of the first embodiment.
Figure 3:
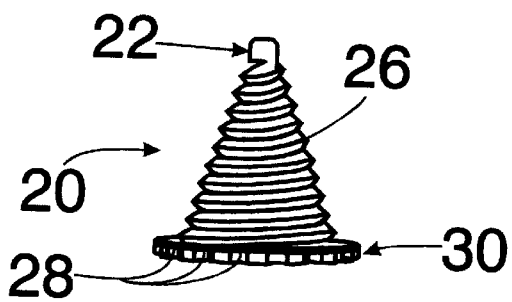
FIG. 3 is side view of the first embodiment.
Figure 4:
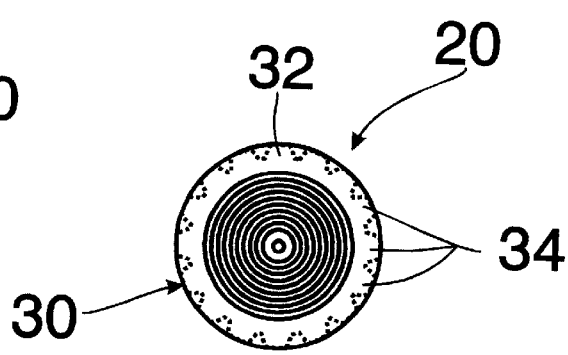
FIG. 4 is a bottom view of the first embodiment.

A first preferred embodiment of the trocar button of the present invention is shown in FIGS. 1–4 generally at 20. Trocar button 20 has a small, cylindrical, barrel-shaped entry tip 22, a conical body portion 24 and an outwardly protruding flange 30. The conical angle of body portion 24 is preferably 45°. Conical body portion 24 has a peripheral thread 26 extending from entry tip 22 to just beneath flange 30. Flange 30 has a maximum diameter of ⅞" from the upper portion of the conical body 24 which has a maximum diameter of ⅝".

The prior art buttons have flanges which protrude only 1/16", or about 16% and, with the overall diameter being only ⅝", the flange does little to enhance grippability of the trocar button. The button 20 of the present invention, on the otherhand, is fully 40% larger which, not only makes it easier to handle, it functions to plug larger openings in the cadaver's skin. This enables the entire operation to be simplified, the incision not having to be quite as carefully made and the larger opening enabling fluid injection/extraction to take place more easily and quickly. The flange 30, which extends between 36 and 40% of the maximum dimension of the conical body portion 24, has a gear tooth pattern 32 formed in its periphery. This gear tooth pattern 32 comprises an external, manually operable drive that permits the button to be more easily gripped and threadably rotated in the opening thereby manually initiating engagement of the threads in the opening (not shown). The corners of the gear teeth 34 are rounded to reduce the risk of sharp corners tearing holes in the protective latex gloves worn by funeral directors during this procedure. In addition, the base of gear teeth 34 are interconnected by a membrane 28 providing a smooth lower surface to flange 30 to prevent teeth 34 from digging into the cadaver's skin. An internal recess 36 is provided to permit a conventional tool (not shown) to finalize the insertion procedure by fully seating flange 30 against the cadaver's skin. Sidewalls 37 taper inwardly to permit them to grip the end of the insertion tool. A pinhole passage 38 (0.050 inch diameter) extends into entry tip 22. Should it be desired to utilize trocar button 20 as a fluid extraction/injection passageway, entry tip 22 can be cut off allowing access into the cavity into which trocar button 20 is installed.

In use, if the trocar button is to be utilized as a fluid passageway, cylindrical barrel-shaped tip 22 is cut off to enable fluid injection/extraction through pinhole 38; in this case, the initial thread 26 performs the lead-in function. If not, tip 22 is inserted in a small incision in the cadaver's skin and threads 26 initially engaged by manually grasping the gear tooth pattern 32 and rotating trocar button clockwise until the flange 30 seats against cadaver's skin. Should rotation become labored/difficult, a conventional tool (not shown) may be inserted in internal drive opening 36 and the trocar button rotated to fully seat flange 30 against the cadaver's skin.

Various changes, alternatives and modifications will become apparent to one of ordinary skill in the art following a reading of the foregoing specification. It is intended that all such changes, alternatives and modifications as fall within the appended claims be considered part of the present invention.

I claim:

1. A trocar button for use in preparing a cadaver for burial comprising
   a) an entry tip;
   b) a conical body portion extending outwardly from a first end of said entry tip, said conical body portion having a threaded eternal peripheral section;
   c) a head section attached to said body portion, said head section having an external, manually-engageable drive including a gear tooth pattern on a periphery of said head section, and an internal drive which may be engaged by a tool, a membrane interconnecting a base portion of adjacent gear teeth to prevent said gear teeth from digging into the cadaver's skin;

whereby said manually-engageable drive may be used to initiate insertion resulting from manual rotation and said trocar button may be fully seated by engaging a tool in said internal drive.

2. The trocar button of claim 1 wherein said said entry tip comprises a barrel-shaped element including a small-diametered cylindrical member terminated by a flat outer surface.

3. The trocar button of claim 1 wherein said external, manually-engageable drive further comprises rounded corners on each tooth of said gear tooth pattern to protect a user's latex gloves from tearing.

4. The trocar button of claim 2 wherein said internal drive comprises a recess which extends through said head section into said conical body portion.

5. The trocar button of claim 4 wherein said recess tapers inwardly as it extends into said conical body portion.

6. The trocar button of claim 5 further comprising a drainage and injection opening which extends from said internal drive recess into at least a portion of said barrel-shaped entry tip.

7. The trocar button of claim 1 wherein said head section further comprises a flange extending laterally outwardly from an upper region of said conical body portion.

8. The trocar button of claim 7 wherein said flange extends outwardly from said conical body portion an amount in the range of between 36 and 40% of a maximum radius of said conical body portion.

9. The trocar button of claim 8 wherein said flange more preferably extends outwardly from said conical body portion an amount equal to 38% of said maximum radius of said conical body portion.

10. The trocar button of claim 1 wherein said conical body portion forms an angle of 45°.

* * * * *